United States Patent [19]

Brown et al.

[11] Patent Number: 5,316,926

[45] Date of Patent: May 31, 1994

[54] METHOD FOR THE MICROBIOLOGICAL PRODUCTION OF NON-ANTIGENIC HYALURONIC ACID

[75] Inventors: Karen K. Brown, Parkville, Mo.; Linda L. C. Ruiz, Haneohe, Hi.; Ivo van de Rijn, Winston-Salem, N.C.; Nathan D. Greene, Leawood, Kans.; Sandy L. Trump, De Soto, Kans.; Curtis D. Wilson, Shawnee Mission, Kans.; Sharon A. Bryant, Shawnee, Kans.

[73] Assignee: Miles Inc., Pittsburgh, Pa.

[21] Appl. No.: 796,178

[22] Filed: Nov. 22, 1991

Related U.S. Application Data

[60] Continuation-in-part of Ser. No. 873,245, Jun. 11, 1986, abandoned, and a continuation-in-part of Ser. No. 910,246, Sep. 18, 1986, Pat. No. 4,782,046, which is a continuation of Ser. No. 801,973, Nov. 26, 1985, abandoned, which is a division of Ser. No. 555,224, Nov. 25, 1983, abandoned.

[51] Int. Cl.$^5$ .................. G12P 19/04; G12N 15/01; G12N 1/20
[52] U.S. Cl. .................. 435/101; 435/172.1; 435/253.4; 435/885; 536/55.1; 536/124
[58] Field of Search .............. 435/101, 885, 172.1, 435/253.4; 536/55.1, 55.2, 123, 124

[56] References Cited

U.S. PATENT DOCUMENTS

| | | | |
|---|---|---|---|
| 2,975,104 | 3/1961 | Warren | 195/28 |
| 3,396,081 | 8/1968 | Billek | 195/7 |
| 4,007,184 | 2/1977 | Cronin | 260/250 Q |
| 4,141,973 | 2/1979 | Balazs | 424/180 |
| 4,303,676 | 12/1981 | Balazs | 424/359 |
| 4,328,803 | 5/1982 | Pape | 128/276 |
| 4,517,295 | 5/1985 | Bracke et al. | 435/101 |
| 4,582,798 | 4/1986 | Brown et al. | 435/68 |

FOREIGN PATENT DOCUMENTS

58-56692  4/1983  Japan .

OTHER PUBLICATIONS

Bergey's Manual of Determinative Bacteriology, 8th ed, 1974, p. 498.
Leuette et al, "Manual of Clinical Microbiology", 1974, pp. 61–62, ASM.
Infection and Immunity, Feb. 1980, vol. 27, No. pp. 444–448, I Van De Rijn "Growth Characteristics of Group A Streptococci in a New Chemically Defined Medium".
J. Gen. Microbiol. 1974 85 Pt. 2, 375-5 "The Capsule of Streptococcus Equi".
ACTA, Path. Microbiol Scand. Sect. B 84, 162–164, 1976 "Isolation of Hyaluronic Acid from Cultures of Streptococci in a Chemically Defined Medium". (CA 85:16770s vol. 85 1976 also enclosed).
Merck Index, 9th Ed. (3re Printing) 1978, p. 537.
The Doctoral Thesis "The Biosynthesis of Hyaluronate by Group A Streptococcus" J. Ginzburg, 1955.
Van de Rijn, Streptococcal Hyaluronic Acid: Proposed Mechanism of Degradation and Loss of Synthesis During Stationary Phase. J. Bact, vol. 156, pp. 1059–1065, 1983.

*Primary Examiner*—Irene Marx
*Attorney, Agent, or Firm*—Joseph C. Gil; Lyndanne M. Whalen

[57] ABSTRACT

The present disclosure is concerned with the production of high molecular weight hyaluronic acid suitable for medicinal administration to mammals without provoking an immune response from microbiological fermentation. The cultures may be prepared from specially developed strains of hyaluronic acid generating bacteria obtained by passaging in serologically negative host animal blood. The cultures are kept in log phase growth for an extended period by appropriate temperature, pH and glucose content adjustments. If the cultured strain is not hyaluronidase negative the hyaluronidase activity is inhibited. The hyaluronic acid is precipitated from the culture by the sequential addition of an anionic surfactant and then a cationic surfactant and extended from the precipitate with a high molarity aqueous calcium ion solution. The isolated aqueous hyaluronic acid solution may then be purified by passage through a nitrocellulose filter. Its pyrogenicity may be alleviated by treatment with a strong acid washed activated carbon.

2 Claims, 4 Drawing Sheets

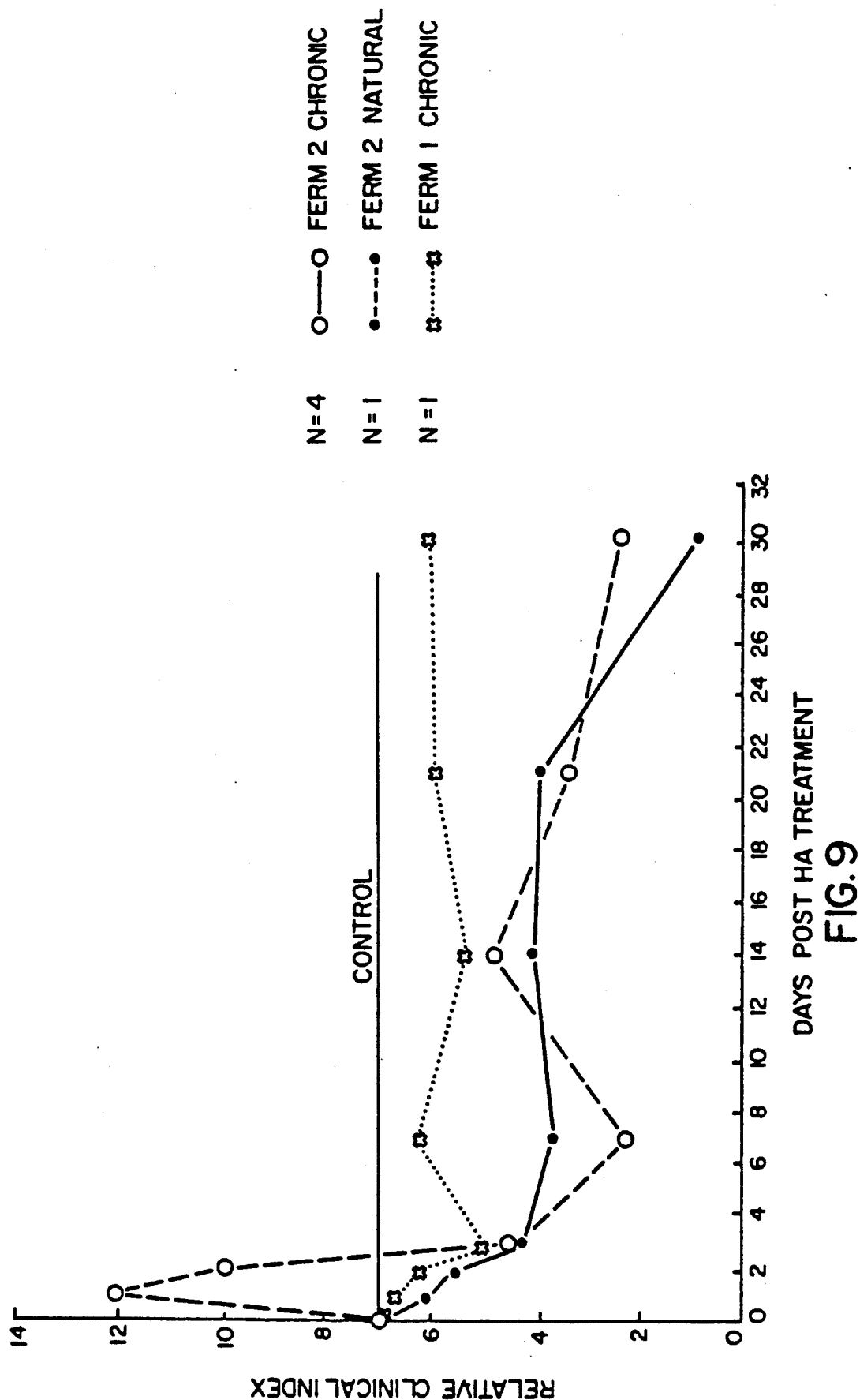

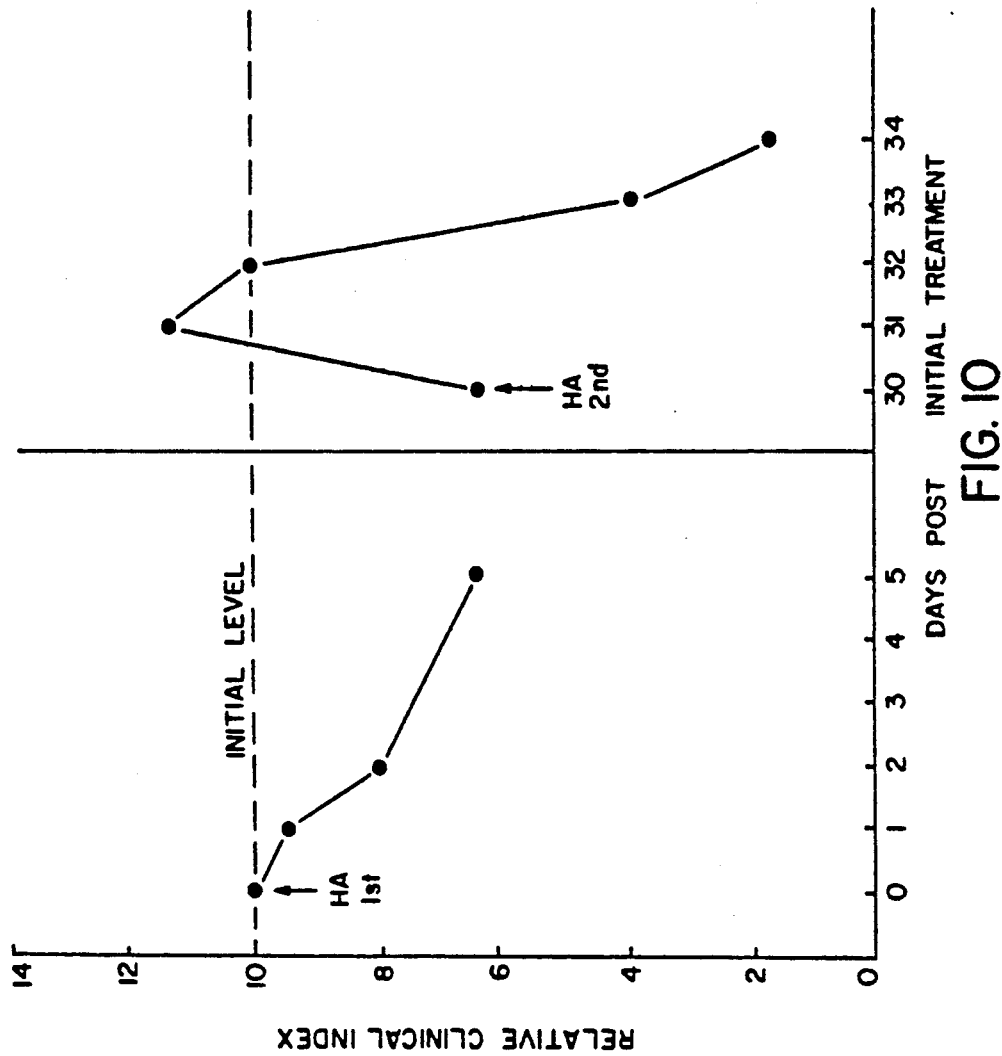

METHOD FOR THE MICROBIOLOGICAL PRODUCTION OF NON-ANTIGENIC HYALURONIC ACID

This present application is a continuation-in-part of U.S. application Ser. No. 06/873,245, now abandoned filed Jun. 11, 1986 and is a continuation-in-part of U.S. Ser. No. 06/910,246, filed Sep. 18, 1986, now U.S. Pat. No. 4,782,046 issued Nov. 1, 1988, which was Rule 60 continuation of U.S. application Ser. No. 06/801,973, filed Nov. 26, 1985, now abandoned, which was a divisional of U.S. application Ser. No. 06/555,224, filed Nov. 25, 1983, now abandoned.

RELATED APPLICATIONS

U.S. patent application Ser. No. 06/555,310, filed Nov. 25, 1983, now abandoned and U.S. application Ser. No. 07/816,548, filed Jan. 6, 1986, now U.S. Pat. No. 5,093,487.

FIELD OF THE INVENTION

This disclosure is concerned generally with the preparation, purification and use of hyaluronic acid and its salts and specifically with the preparation of hyaluronic acid from a microbiological source.

BACKGROUND OF THE INVENTION

Hyaluronic acid is a naturally occurring high molecular weight polysaccharide typically recovered as its sodium salt having an empirical formula of $(C_{14}H_{20}N Na O_{11})_n$ where $n > 1000$. The general structure of hyaluronic acid is illustrated in Merck Index, Ninth Ed. (3rd printing, 1978), at page 624. It is well known that hyaluronic acid and its salts, hereafter collectively referred to as HA, can be obtained from at least three sources: human umbilical cords, rooster combs and certain bacterial cultures such as group A and C hemolytic streptococci. However, certain disadvantages are associated with the former two sources (e.g. relatively low yields, contamination with chondroitin sulfate, and labor intensive processing and purification steps).

Since HA is found in aqueous and vitreous humor of eyes and the synovial fluid of mammalian joints, there has been considerable interest in obtaining purified HA for use as a fluid replacement to correct pathological conditions in the eye and in joints. The preparation of HA from rooster combs and human umbilical cords and its use in eye and joint applications is described in U.S. Pat. No. 4,141,973 to E. A. Balazs. That patent also provides a detailed review of the technical literature describing the isolation, characterization and uses of HA.

U.S. Pat. No. 4,303,676, also to E. A. Balazs, describes cosmetic formulations containing sodium hyaluronate fractions in various molecular weight ranges made from rooster combs. U.S. Pat. No. 4,328,803 to L. G. Pape discloses the use of an ultrapure hyaluronic acid salt in eye surgery. The HA product used was a sodium hyaluronate salt available under the registered trademark HYLARTIL B ® from Pharmacia, Inc. and obtained in commercial quantities from rooster combs.

Because the medical applications of HA require that the HA be injected into a mammalian body (e.g. as a fluid replacement), it is very important that the injected products be as pure as possible to avoid reactivity problems. This importance of purity is described in U.S. Pat. No. 4,141,973 which describes an ultrapure HA product prepared from rooster combs or, alternatively, from human umbilical cords. In addition to purity, it appears that control of molecular weight of an HA product is very important (e.g. the U.S. Pat. No. 4,141,973 suggests an average molecular weight of at least 750,000 daltons and U.S. Pat. No. 4,303,676 suggests having two distinct fractions of controlled molecular weight, one low and one high). Although there is a description of a high molecular weight (1,200,000 daltons) HA preparation of very high purity (i.e. less than 0.05% protein) in a paper by Swann, Arch. Opthal. 88, pp. 544–8 (1972), we are unaware of any description of an HA product having the following advantages: (1) derivable from a microbiological source at relatively low costs, in high yields, and with low reactivity upon injection; (2) having a desirably high and closely controlled average molecular weight; and (3) being substantially free of protein and nucleic acid impurities.

The microbiological production of hyaluronic acid is well known in the literature. A rather extensive discussion is found in "The Biosynthesis of Hyaluronate by Group A Streptococci", a 1955 doctoral thesis on file at The University of Minnesota. Japanese Published Patent Application 83-56692 teaches greatly enhancing the production of hyaluronic acid from *Streptococcus zooepidemicus* and *Streptococcus equi* cultures by adding high levels of glucose to a protein (yeast extract) containing culture and continuously aerating while shaking. Although a 1976 paper of Kjem in *Acta. Pathol. Microbial Scand.* is acknowledged as teaching microbiological production of hyaluronic acid no explicit mention of a chemical defined medium (CDM) or a protein free medium is made. There is no indication that its technology could be applied to such a specialized medium. U.S. Pat. No. 2,975,104 to Warren teaches a technique for increasing the acceptable incubation time of streptococci in producing hyaluronic acid by the use of a particular medium which contains a hyaluronidase inhibitor. The growth of Group A streptococcal strains in a chemically defined medium (CDM) with the production of a hyaluronic acid capsule is disclosed in "Growth Characteristics of Group A Streptococci in a New Chemically Defined Medium" by Van de Rijn and Kessler at pages 444 to 448 of Volume 27, Number 2 (February 1980) of Infection and Immunity. The recovery of hyaluronic acid from a somewhat different CDM by heat killing the culture, filtering the medium, precipitating with ethanol, centrifuging the precipitate, suspending the precipitate in an aqueous sodium chloride solution, reprecipitating with cetyl pyridinium chloride, centrifuging the reprecipitate, dissolving this reprecipitate in an aqueous sodium chloride solution and finally precipitating once again with ethanol is described in "Isolation of Hyaluronic Acid from Cultures of Streptococci in a Chemically Defined Medium" by Kjems and Lebech at pages 162 to 164 of Section B, Volume 84 (1976) of *Acta Path. Microbial. Scand.* This procedure has some significant disadvantages. The heat killing of the microorganisms will result in the hyaluronic acid's becoming unnecessarily contaminated with proteins, nucleic acids and other internal cell components which are difficult to separate from the hyaluronic acid and can provoke immune reactions in mammals. Thus, some of the benefit of utilizing a chemically defined medium to avoid protein contamination and achieve nonantigenicity is unnecessarily lost as compared to the contamination suffered merely from the natural death of cells in a growing culture. Furthermore, this CDM itself has limited utility because it will not support the growth of most streptococcal strains. The recovery of hyaluronic acid of a mean molecular weight of about 55,000 daltons from an anaerobically grown culture of *Streptococcus pyogenes* inactivated with trichloroacetic acid by filtering using a 0.22 micrometer pore size, disfiltering with a filter having a nominal retention of 30,000 daltons molecular weight until the conductivity of the filtrate is 0.5 mesa-ohms (believed to mean inverse ohms per centimeter times 10), precipitating with ethanol, resuspending in an aqueous sodium chloride solution, precipitating with CETAB (believed to be hexadecyl trimethyl ammonium bromide), coarse filtering, resuspending in an aqueous sodium chloride solution and disfiltering with a filter having a nominal molecular weight retention of 30,000 daltons until the conductivity is "0.5 mesa-ohms" is described in U.S. Pat. No. 4,517,295 to Bracke and Thacker. This procedure also involves the troublesome killing of the culture cells. In this case, the trichloroacetic acid not only kills these cells with the resultant contamination problem, but it also is relied on for an effective separation of the cells from the broth. Furthermore, this broth is only semi-defined and contains casein derived proteins which may also contaminate the obtained hyaluronic acid.

Non-antigenic hyaluronic acid is also discussed in the literature. A process of obtaining hyaluronic acid free from proteins, antigens and pyrogens by treating an aqueous alkaline suspension to denature the protein, subjecting the suspension under appropriate conditions to proteolytic ferments, removing amino acids and mineral salts with ion exchangers, and aciditying to pH 3 to 4 to precipitate the remaining impurities with some of the hyaluronic acid is described in U.S. Patent No. 3,396,081 to Billek. A reportedly ultrapure hyaluronic acid suitable for injection into the human eye or animal joints and obtained by an involved extraction procedure including a five day chloroform extraction under mixing is described in U.S. Pat. No. 4,141,973 to Balazs.

A useful procedure for the isolation of hyaluronic acid capsules from streptococci cultures by incubating the bacteria, which had already been isolated by centrifugation and washed with saline, with sodium dodecyl sulfate in a saline suspension until the capsule was released, centrifuging to recover the supernatant, filtering the supernatant through a 0.22 micrometer pore filter, precipitating the hyaluronic acid with hexadecyltrimethyl ammonium bromide, recovering the precipitate by centrifugation, redissolving the precipitate in 2M calcium chloride and clarifying the solution by centrifugation, precipitating with ethanol, redissolving with water followed by the addition of sodium chloride and clarifying the solution by centrifugation, and repeating the ethanol precipitation five times is described in "Streptococcal Hyaluronic Acid: Proposed Mechanism of Degradation and Loss of Synthesis During Stationary Phase" by Van de Rnn at pages 1059 to 1065 of volume 156, number 3 (December, 1983) of the Journal of Bacteriology. The use of sodium dodecyl sulfate to separate another virulence factor, M-protein, from *Streptococcus equi* is discussed in U.S. Pat. No. 4,582,798 to Brown, Bryant and Lewis. These latter two developments became publicly available after many of the developments with which the present disclosure is concerned.

There is a need for an efficient and inexpensive procedure to obtain high molecular weight hyaluronic acid suitable for injection into mammals. A microbiological fermentation which gives high yields of a relatively uncontaminated high molecular weight hyaluronic acid and a recovery procedure which does not create unnecessary purification problems and does not adversely affect the molecular weight of the hyaluronic acid are both desirable and would meet this need.

BRIEF DESCRIPTION OF FIGURES

FIGS. 8–9 are graphs comparing the efficacies as a joint fluid replacement of the HA products of this disclosure with controls and/or, a commercially available product.

FIG. 10 is a graph showing the use of the product of this disclosure as a fluid replacement in an equine joint diseased by unspecified cause.

SUMMARY OF THE INVENTION

Figure 1:
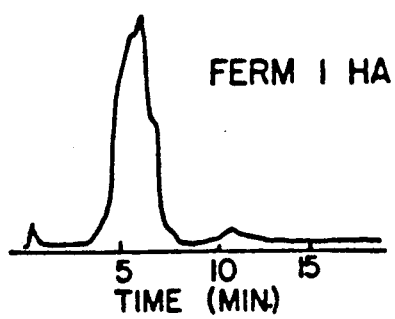
FIGS. 1–4 are graphs showing HPLC determined molecular weight distributions (retention times) of HA made from four microbiological fermentations in accordance with the disclosures herein.
Figure 2:
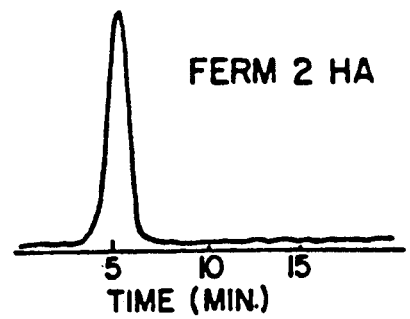
Figure 3:
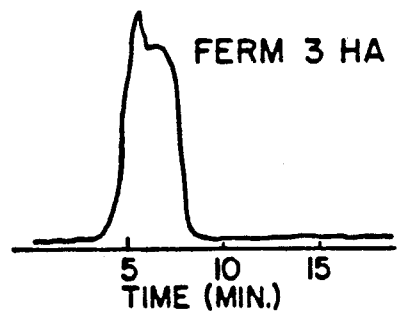
Figure 4:
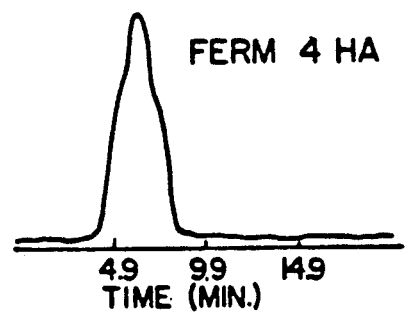

A procedure for culturing suitable microorganisms to give high yields of high molecular weight antigen-free hyaluronic acid by growing these organisms in a chemically defined medium free of protein, keeping them in log phase growth by appropriate pH control and addition of dextrose (glucose) for an extended period, and isolating the hyaluronic acid without killing the microorganisms has been developed. The microorganisms are suitable if they produce extracellular hyaluronic acid capsules and either do not produce extracellular hyaluronidase or are grown in a medium treated by heat or an appropriate chemical agent to inhibit the activity of hyaluronidase. A procedure for separating hyaluronic acid capsules from the cells which produced them by treatment with an anionic surfactant has also been developed. Also developed is a procedure of isolating hyaluronic acid from the bacterial culture which produced it by sequential treatment with an anionic surfactant and then a cationic surfactant. Additionally developed is a procedure for isolating hyaluronic acid from anionic/cationic surfactant complexes by dissolving it in a high molarity aqueous solution of a calcium ion such as calcium chloride. Another development is the reduction of the protein content of an aqueous hyaluronic acid solution by passing it through a nitro cellulose filter. An additional development is the removal of pyrogens from high molecular weight hyaluronic acid by treating an aqueous solution of it with strong acid washed activated carbon. A preferred procedure is to combine some or all of the above developments with dissolution in water and precipitation in a lower alcohol, such as ethanol or isopropanol, to obtain high yields of a pyrogen free very pure high molecular weight hyaluronic acid. An especially preferred procedure is to apply these developments in such a way as to obtain a high molecular weight hyaluronic acid which as an approximately 1 weight percent aqueous solution has a protein content of less than about 1.25 mg/ml, preferably 0.10 mg/ml, and a nucleic acid content of less than about 0.045 mg/ml, preferably 0.005 mg/ml, as determined by UV absorbance at 280 and 257 nanometers, respectively. It is further preferred to apply these developments so as to obtain hyaluronic acid which displays a single significant substantially symmetrical HPLC retention peak with retention times representative of molecular weights between about 1,100,000 and 4,000,000 daltons and with at least 98% of the distribution lying within this single peak. It is particularly preferred to utilize the extraction and purification developments to obtain a hyaluronic acid which as an approximately 1 weight percent aqueous solution has an amino acid content by orthophthalaldehyde fluorescence (which inherently involves the hydrolysis of any protein present back to its constituent amino acids) of less than about 0.4 mg/ml and a nucleic acid content by ethidium bromide fluorescence of less than about 0.06 mg/ml and which has a standardized FPLC determined average molecular weight of at least about 1,100,000 daltons.

A hyaluronic acid which has a high molecular weight, a narrow molecular weight distribution and a very high purity has also been developed. The process developments have enabled the recovery and purification of hyaluronic acid without the significant loss of molecular weight and without substantial broadening of the molecular weight distribution. A preferred hyaluronic acid is pyrogen free, has a single substantially symmetrical HPLC retention peak lying between retention times representative of molecular weights between about 1,100,000 and 4,000,000 daltons with about 98% of the distribution encompassed by this peak and has a UV absorbance determined protein content of less than about 1.25 mg/ml and a UV absorbance determined nucleic acid content of less than about 0.045 mg/ml, both determined on a one weight percent aqueous solution.

Finally, a technique for creating strains of hyaluronic acid generating bacteria especially suitable for the production of hyaluronic acid by passaging it through the blood of an animal which is susceptible to the bacteria but has not developed an immune response to the bacteria has been developed. A preferred procedure is to passage a *Streptococcus equi* strain through horse blood which gives no evidence, such as a detectable antibody level, of prior exposure to this bacterium. A strain was developed in accordance with this technique and is on deposit with the American Type Culture Collection (ATCC) under number 39,506.

DETAILED DESCRIPTION OF THE INVENTION

The maintenance of hyaluronic acid generating microorganisms in the log or exponential growth phase for extended periods is achieved by careful pH and temperature control and periodically supplementing the culture with additional dextrose. Neither shaking nor continuous aeration are required. This procedure would, of course, be futile unless either the particular microorganism was hyluronidase negative, i.e. it did not generate extracellular hyluronidase, or the activity of any such extracellular hyaluronidase had been inhibited by heat treatment or a chemical inhibitor such as those taught in U.S. Pat. No. 2,975,104 to Warren. It is preferred to conduct this growth in a chemically defined media such as that taught in "Growth Characteristics of Group A Streptococci in a New Chemically Defined Medium" by Van De Rijn and Kessler at pages 444 to 448 of Volume 27, Number 2 (February 1980) of *Infection and Immunity* so as to avoid the presence of extraneous protein. This simplifies the subsequent purification since only the proteins released from the microorganism being cultured then need to be removed.

The preferred growth medium is the chemically defined medium of Van De Rijn referred to above. This medium is prepared from the following components in the amounts indicated:

| Group 1 | |
|---|---|
| $FeSO_4.7H_2O$ | 5 mg/l |
| $Fe(NO_3)_2.9H_2O$ | 1 mg/l |
| $K_2HPO_4$ | 200 mg/l |
| $KH_2PO_4$ | 1000 mg/l |
| $MgSO_4.7H_2O$ | 700 mg/l |
| $MnSO_4$ | 5 mg/l |
| Group 2 | |
| DL-Alanine | 100 mg/l |
| L-Arginine | 100 mg/l |
| L-Aspartic Acid | 100 mg/l |
| L-Cystine | 50 mg/l |
| L-Glutamic Acid | 100 mg/l |
| L-Glutamine | 200 mg/l |
| Glycine | 100 mg/l |
| L-Histidine | 100 mg/l |
| L-Isoleucine | 100 mg/l |
| L-Leucine | 100 mg/l |
| L-Lysine | 100 mg/l |
| L-Methionine | 100 mg/l |
| L-Phenylalanine | 100 mg/l |
| L-Proline | 100 mg/l |
| Hydroxy-L-proline | 100 mg/l |
| L-Serine | 100 mg/l |
| L-Threonine | 200 mg/l |
| L-Tryptophan | 100 mg/l |
| L-Tyrosine | 100 mg/l |
| L-Valine | 100 mg/l |
| Group 3 | |
| p-Aminobenzoic Acid | 0.2 mg/l |
| Biotin | 0.2 mg/l |
| Folic acid | 0.8 mg/l |
| Niacinamide | 1.0 mg/l |
| $\beta$-Nicotineamide adenine dinucleotide | 2.5 mg/l |
| Pantothenate calcium salt | 2.0 mg/l |
| Pyridoxal | 1.0 mg/l |
| Pyridoxamine di-hydrochloride | 1.0 mg/l |
| Riboflavin | 2.0 mg/l |
| Thiamine hydrochloride | 1.0 mg/l |
| Vitamin $B_{12}$ | 0.1 mg/l |
| Group 4 | |
| Glucose | 10,000.0 mg/l |
| Group 5 | |
| Adenine | 20 mg/l |
| Guanine hydrochloride | 20 mg/l |
| Uracil | 20 mg/l |
| Group 6 | |
| $CaCl_2.6H_2O$ | 10 mg/l |
| $NaC_2H_3O_2.3H_2O$ | 4,500 mg/l |
| L-Cysteine | 500 mg/l |
| $NaHCO_3$ | 2,500 mg/l |
| $NaH_2PO_4.H_2O$ | 3,195 mg/l |
| $NaH_2PO_4$ | 7,350 mg/l |

The above-listed components were added in groups. Each group was dissolved completely before addition of the next. The purines and pyrimidines of Group 5 were dissolved in 2N HCl at 500×concentration and diluted to 100×with distilled water before use or storage at −20° C. Each component in Group 6 was added separately. The final pH of the medium was between 6.95 and 7.05.

The temperature and pH of the culture should be maintained in the range known to be conductive to the growth of the particular microorganism being cultured. In the case of Groups A and C streptococci, which are preferred microorganisms, the temperature is advantageously around 37° C. and the pH should be maintained in the range of about 7 and slightly above. In the case of the particularly preferred Group C streptococci and the most preferred *Streptococcus equi* the pH is preferably maintained between about 7.0 and 7.2 and the temperature is preferably about 37° C. Culturing for between about 24 and 120 hours under these conditions has been found to be advantageous. The pH control may be continuous or it may be intermittent. In the latter case the pH may be readjusted each time dextrose is added. For the Group C streptococci including the *Streptococcus equi* it is preferred to readjust the pH to about 7.6 at each dextrose addition.

Sufficient dextrose should be added to the microorganism on a timely enough regimen to avoid complete depletion of the dextrose from the culture medium. The microorganism utilizes the dextrose in synthesizing its hyaluronic acid capsule and thus continuously consumes dextrose from the medium. In the case of the streptococci, especially the Group C and most especially the *Streptococcus equi* addition on no more than a twenty-four hour interval is preferred. With these bacteria it is preferred to add approximately 1 weight percent of dextrose, based on the total weight of the culture including medium. An especially preferred procedure with these bacteria is to add 1 weight percent dextrose every twenty-four hours but to also add an additional 0.5 weight percent of dextrose between the larger additions, preferably about sixteen hours after the 1.0 percent addition.

The recovery of hyaluronic acid is enhanced if the pH control is discontinued sufficiently before it is to be harvested to cause a significant pH drop. A drop to a value of between about 6.5 and 6.8 is preferred. A desirable drop can be obtained by ceasing pH control about 12 hours before harvest although ceasing between about 6 and 12 hours before harvest has been found suitable. Such a procedure facilitates centrifugation and increases the yield of hyaluronic acid.

The ability to maintain the microorganism in log phase growth is surprising and makes it possible to continuously culture the microorganism. In such a procedure once some of the nutrients other than the rapidly consumed dextrose become exhausted, the depleted medium may be separated from the cells of the microorganism and replaced with a freshly constituted medium. Alternatively, the depleted nutrients can be added to the medium in appropriate amounts. However, at some point, the waste products and the hyaluronic acid not attached to the cells need to be extracted from the culture. One convenient technique is simply to filter the medium using a pore size which retains the cells. Then the cells can be provided with fresh medium and hyaluronic acid can be extracted from the depleted medium.

In preparing the initial medium and, in the case of continuous culturing, in preparing a replacement medium it is preferred to sterilize the medium to avoid the presence of undesirable microorganisms. A convenient technique for such a sterilization is to pass the medium through a fine pore filter, such as a 0.22 micrometer pore filter.

In initiating the culture, it is also convenient to use an inoculation seed grown on the same CDM as the growth medium and to use between about 1 and 5 volume percent of inoculate. If the CDM described by Van De Rijn and Kessler, Supra, is used it is also convenient to add the cysteine and bicarbonate of soda to the medium just before inoculation. These two nutrients have a tendency to form salts which can precipitate out of the medium.

The separation of hyaluronic acid, especially in capsular form, from the cells of the microorganism which generated it is conveniently affected by incubation with an anionic surfactant. Among the suitable surfactants are those compounds which are available in sufficient purity to use in such a fermentation bath and which carry one or more sulfate or sulphonate groups. Among the particularly preferred surfactants are sodium dodecyl sulfate and dioctyl sodium sulfosuccinate, with the former being especially preferred. The amount of surfactant required is dependent on the hyaluronic acid content of the culture and is generally at least about 0.01 weight percent based on the weight of the culture. In the case of Group C streptococci and sodium dodecyl sulfate at a 0.01 wt. % level, an incubation time at 37° C. of about 15 minutes has been found to be beneficial. In the case of microorganisms force grown, i.e. kept in log phase, for an extended period the increased content of hyaluronic acid requires a higher content of surfactant. For cultures containing between about 1 and 2.5 grams of hyaluronic acid per 10 liters a surfactant content in the neighborhood of 0.1 weight percent is usually found suitable. A suitable range for such high yield culture is between about 0.05 and 0.25 weight percent, based on the weight of the culture including the medium. The separated hyaluronic acid can then be isolated from the culture by any suitable means including filtration to remove the larger cells and disfiltration to remove the lower molecular weight species. A particularly preferred technique is to precipitate the hyaluronic acid and anionic surfactant by the addition of a cationic surfactant.

The isolation of hyaluronic acid from the medium in which it is grown can be effected by the sequential addition of an anionic surfactant followed by the addition of a cationic surfactant. The suitable types and amounts of the anionic surfactant are discussed hereinabove. The cationic surfactant is preferably an ammonium salt and more preferably a quaternary ammonium salt. Especially preferred are quaternary ammonium salts with four aliphatic substituents particularly those in which at least one of the substituents is a long hydrocarbon chain. Among these long chain substituted aliphatic quaternary ammonium salts hexadecyl trimethyl ammonium bromide is particularly preferred. A preferred technique for precipitating the hyaluronic acid is to cross titrate the anionic and cationic surfactants in samples of the culture until a heavy readily separable flock is obtained. A convenient manner to accomplish this cross-titration is to prepare numerous one milliliter samples of culture at each of several levels of anionic surfactant, for example at levels between 0.05 and 0.25 weight percent in 0.05 percent steps, and then add various amounts of the cationic surfactant to the samples for each level of anionic surfactant, for example amounts between 10 and 100 microliters of a 10% solution may be added in 10 microliter steps. As a double check after the appropriate amount of anionic surfactant has been added to the total culture a sample may be titrated against the cationic surfactant to confirm the appropriate level to be added.

The anionic surfactant is thoroughly mixed and incubated with the culture before the addition of the cationic surfactant. In general, a mixing time of at least about fifteen minutes is preferred with a mixing time of at least thirty minutes being more preferred, especially with culture volumes in the neighborhood of 2000 liters or more.

It has been found advantageous to use a 10 percent aqueous solution of hexadecyl trimethyl ammonium bromide to precipitate the hyaluronic acid from a ten liter culture to which at least about 0.01 weight percent of sodium dodecyl sulfate had been added and mixed for at least fifteen minutes. It was found that between about 100 and 400 milliliters of this solution was suitable and that at least about one hour should be allowed for maximum floc formation.

The precipitate formed by the sequential addition of anionic and cationic surfactants may be separated from the balance of the culture by any common liquid solid separation technique. Among the convenient and preferred techniques are filtration and centrifugation. It is preferred to cool the entire medium below the growth temperature and preferably below about 10° C. and to store it for an extended period, in the case of 2000 liter or larger cultures for in excess of sixteen hours, before effecting this separation. The most preferred separation technique is centrifugation. Utilizing such a procedure resulted in a supernatant almost completely free of hyaluronic acid.

Hyaluronic acid may be separated from an anionic/cationic surfactant complex by dissolution in a high molarity aqueous solution of a calcium ion. A preferred solvent is a 2M solution of calcium chloride. It is preferred to use a reduced volume of solvent compared to the original culture and between about 5 and 10 volume percent has been found suitable although between about 10 and 40 volume percent is preferred. The solution is preferably carried out at temperatures between about 4° and 30° C. with temperatures between about 4° and 10° C. being preferred for a period of at least 6 hours with periods of between about 1 and 10 days being preferred for original cultures of 2000 liters or greater.

The dissolved hyaluronic acid can now be isolated from the surfactant complex and other materials which precipitated with the surfactant complex by any typical solid/liquid separation technique including filtration or centrifugation. Centrifugation is particularly preferred.

The hyaluronic acid can then be purified by a variety of techniques which involve precipitation in a lower alcohol followed by resolution in water. Particularly suitable alcohols are ethanol and isopropanol.

The protein and nucleic acid content of the hyaluronic acid can be significantly reduced by passing an aqueous solution of it through a nitrocellulose filter. It is preferred to conduct at least one and preferably several ethanol precipitations and subsequent water resolutions before effecting this filtration step. This will reduce the protein load on the filter matrix and reduce the probability that it will become saturated with protein. The pore size of the filter is not critical but is somewhat dependent on the viscosity of the solution being filtered. Pore sizes from 0.22 micrometers to 25 micrometers may readily be utilized with pore sizes of 8 micrometers and greater being preferred for the more viscous solutions to minimize the back pressure. With a single thickness of a standard nitrocellulose filter it is preferred to utilize no more than about 20 mg/cm$^2$ of protein per unit area of filter with a ratio of no more than about 10 mg/cm$^2$ being more preferred and a ratio of no more than about 2 mg/cm$^2$ being especially preferred. Although nitrocellulose is known to have affinity for nucleic acids it is surprising that it is able to extract both nucleic acids and protein from an aqueous solution of hyaluronic acid, which itself is known to have an affinity for these materials. There does not appear to be any basis for predicting that the equilibrium between water and nitrocellulose, let alone water containing an attractant for protein, would lead to substantial extraction of protein. In this regard treating a 4.5 liter solution by passage through an approximately 670 cm$^2$ nitrocellulose filter resulted in an about 78% reduction in protein from 0.028 wt. % to 0.006 wt. Such an equilibrium partitioning was totally unpredictable.

Further filter thicknesses proportionally increase the protein per unit area of filter which can be removed. For instance with two thicknesses, it is preferred to utilize no more than about 15 mg/cm$^2$ of protein per unit filter area.

Hyaluronic acid may be freed of pyrogens by contact as an aqueous solution with acid washed activated carbon. The pyrogenic agent is evidently independent from the protein and nucleic acids which may provoke an immune response in a mammal. A pyrogenic response has been detected in rabbits injected with hyaluronic acid which has a very low amino acid content (by the orthophthalaldehyde fluorescence which hydrolyzes any proteins present and detects them as their constituent amino acids) and a very low ethidium bromide fluorescence detected nucleic acid content. This response was observed using the established protocol of injecting into the ear vein of a frequently handled rabbit and observing any resultant increase in body temperature. A rise of greater than 0.6° C. or a total rise of greater than 1.2° C. from this rabbit and two additionally injected rabbits is an indication of pyrogenicity. When the same batch of hyaluronic acid is tested according to the same protocol after exposing it to a strong acid washed carbon no pyrogenic indication was observed. It is preferred to use sufficient activated carbon to give 2000 preferably 10,000 and most preferably 20,000 m$^2$ of surface area per liter of aqueous 1 weight percent solution being treated. An especially preferred technique is to utilize a fairly high surface area activated carbon of more than about 500 m$^2$/g and to utilize in excess of about 10 grams per liter of one weight percent aqueous hyaluronic acid solution.

The acid washed active carbon treatment can be either continuous or batch. In the former case, treatment may conveniently be effected by circulation through a cartridge. In either case treatment can be repeated until negative pyrogenicity is achieved. In view of the minimal amount of pyrogen present, typically in the nanograms per milliliter range, the concern is not saturation of the adsorbent but rather adequate contact with the pyrogen.

The aqueous hyaluronic acid solution obtained by the use of the calcium ion treatment of the anionic/cationic surfactant precipitant may be further purified by repeated precipitations into a lower alcohol, such as ethanol or isopropanol and resolutions in water. In a preferred procedure the supernatant from the calcium ion treatment (preferably a 2M aqueous calcium chloride solution) is extracted with 2 volumes of a suitable alcohol, preferably 95% ethanol or 97% isopropanol and centrifuged or sieve filtered after at least one hour. Then this precipitate is solubilized overnight at between about 4° and 10° C. in deionized, distilled water using between about 1/10 and 1/20 of the original volume and the precipitate is removed by sieve filtration or centrifugation. This is followed by the addition of sufficient sodium chloride to give a one percent solution by weight, i.e. 10 grams per liter of solution. This solution is then extracted with two volumes of an appropriate alcohol to reprecipitate the hyaluronic acid (actually at this point more precisely sodium hyaluronate). The precipitate is then isolated by either sieve filtration or centrifugation. The resolution in water, addition of sufficient salt (sodium chloride) to give 1% (10 grams per liter) and precipitation with two volumes of an appropriate alcohol are continued until the aqueous solution is clear using increasingly smaller volumes of water with each resolution and consequently smaller volumes of alcohol (twice the volume of the solution being extracted). This typically requires four additional alcohol precipitations. An outline of this procedure is as follows:

OUTLINE OF PROCESS FOR EXTRACTION OF BACTERIAL HYALURONIC ACID

1. Grow Streptococcus organism
2. 1 ml/l SLS 10%.
3. 10–40 ml/l.
   Hexadecyltrimethylammonium bromide 10%.
4. Collect ppt.
5. Solubilize in 2M $CaCl_2$.
6. Collect supernatant.
7. 2 Vol. alcohol
   (ppt. HA, some nucleic acids, some protein).
8. Collect ppt.
9. Solubilize ppt. in $DI-H_2O$.
10. Discard undissolved ppt.
11. Collect supernatant.
12. 1% NaCl
    2 Vol. alcohol
    (ppt. HA).
13. Collect ppt.
14. Solubilize in $DI-H_2O$.
15. Discard ppt.
    Collect supernatant.
16. 1% NaCl
    2 Vol. alcohol
    (ppt. HA).
17. Collect ppt.
18. Solubilize in $DI-H_2O$.
19. Discard ppt.
    Collect supernatant.
20. Filter—protein binding type (e.g., nitro-cellulose) (remove some of the minimal protein remaining.
21. 1% NaCl
    2 Vol. alcohol
    (ppt. HA).
22. Collect ppt.
23. Solubilize 0.15M phosphate buffered saline pH 7.2.
24. Adjust to 1% HA by spectrophotometric assay.
25. Sterilize with 0.1% beta-propiolactone
    4°–10° C. 24–48 hours.
26. Hydrolyze beta-propiolactone
    37° C. 24–48 hours.
27. Fill syringes.

The final steps of product preparation may involve washing with 95% ETOH and 99% acetone followed by drying under vacuum. The dried HA is resuspended in 0.15M sodium phosphate buffer to a concentration of 1.0%. This may be filter sterilized through a final 0.45 micrometers nitrocellulose type filter and/or sterilized in final bulk form with 0.1% beta-propiolactone. The beta-propiolactone sterilization is conducted at 4° C, for 24–48 hours followed by hydrolization of the beta-propiolactone at 37° C. for 24–48 hours. The final product contains 10 mg/ml HA in 0.15M sodium phosphate buffer. When these steps are followed, HA of the highest purity is obtained in high yield (99.90% HA).

A more preferred procedure to isolate sodium hyaluronate from the supernatant of the calcium ion treatment involves the use of disfiltration, and reverse precipitation with a winding device. This supernatant may be disfiltered against a membrane which allows species with molecular weights less than about 100,000 to pass through. The water to the feed side of the membrane may then be cut off and water flow on the pass side of the membrane continued until the volume is between about 10 and 40% of the initial volume. This typically gives a hyaluronic acid (or calcium hyaluronate) concentration of between about 0.4 and 0.7 weight percent. This is followed by three ethanol precipitations with a winder apparatus and resolutions utilizing the procedure described in copending U.S. patent application Ser. No. 816,548 filed Jan. 6, 1986. In particular, the sodium chloride content of this disfiltered concentrate is adjusted to ten grams per liter and it is fed to three volumes of 95% ethanol in which a device with vertical fingers is slowly rotating. The precipitating sodium hyaluronate attaches itself to these moving "fingers". The precise configuration and speed of rotation of this "winder" is adapted to the particular vessel used and the batch size but a cage like general configuration is preferred. The ethanol is then drained from the vessel and the precipitated hyaluronate is redissolved by the addition of water to the vessel. The winder should preferably be rotated for at least about 30 minutes after the last of the disfiltered hyaluronate solution is added and may also be rotated after the water addition to aid in resolution. The third resolution may conveniently be in the final desired product formulation buffer such as an aqueous 0.15M sodium phosphate solution. In such a case it is advisable to assay the hyaluronate after the second resolution.

The fairly pure sodium hyaluronate solution may now be further purified and sterilized. In this regard, it is convenient to drop the viscosity of the solution in accordance with copending U.S. patent application Ser. No. 816,548 filed Jan. 6, 1986. In particular, it may be heat treated, preferably at a temperature in excess of about 50° C. for in excess of about 72 hours in an open vessel, or forced through a filter with a pore size less than about one micrometer, until the 37° C. viscosity is less than about 250 centistokes. At this point, the solution may be conveniently tested for pyrogenicity in rabbits and, if a positive result is obtained, appropriately treated with strong acid washed activated carbon. Finally, the now low viscosity pyrogen free solution may be filtered through a 0.45 or 0.22 micrometer pore nitrocellulose filter for both sterilization and final protein and nucleic acid reduction.

The former procedure was used to obtain sodium hyaluronate for further evaluation. The material from four different fermenters was initially evaluated after solubilization in the 2M calcium chloride. One of these lots was then further purified in accordance with this procedure and evaluations made at various stages.

The typical 10 l fermenter of *Streptococcus equi* produces 5 g to 7 g dry weight of cells and 1.0 g to 2.5 g dry weight of HA. Yield is therefore between 14.3% and 50% (W/w). Yields of HA from extraction of rooster combs as in U.S. Pat. No. 4,141,973 are reportedly around 0.079%.

It should be noted that a latter-stage filtration through a suitable protein-binding filter (for example a nitrocellulose filter) is necessary in order to remove reactivity of the final product HA. Other types of filters (plain cellulose and cellulose acetate) do not adequately remove reactivity as observed in the horse joint injection test. It is thought that this step removes the minute quantity of reactive proteinaceous material remaining in the HA.

The purity of this bacterial-derived HA was determined via a colorimetric protein assay, U.V. spectrophotometry, HPLC, and slab gel electrophoresis. Initial experiments involved quantitation of protein contamination as measured via the BIO RAD Protein Assay. This method can detect levels of protein as low as 200 μg/ml. Table I lists the results of testing aqueous 1.0% solutions of hyaluronic acid extracted from four different fermenters of *Streptococcus equi*.

TABLE I

BIO RAD Protein Assay Results

| Sample | O.D. at 595 nm | Concentration of Protein |
|---|---|---|
| Ferm 1 | 0.00,0.000 | <200 μg/ml |
| Ferm 2 | 0.00,0.010 | <200 μg/ml |
| Ferm 3 | 0.00,0.005 | <200 μg/ml |
| Ferm 4 | 0.00,0.005 | <200 μg/ml |

According to such data, the protein content of a 1.0% bacterial-derived HA solution may be as high as 0.02%.

A second method of determining protein, peptide, and/or amino acid content is UV absorption at 280 nanometers. A known concentration of bovine serum albumin was used as a control. Table II reports these results. Also reported are the UV absorptions of some comparative solutions at 257 nm. Absorption at 257 nm represents contamination with nucleotides or nucleic acid such as DNA and RNA. It is noted that spectrophotometric absorption at 280 nm detects more protein contamination than the BIO RAD assay. The 1.0% solutions of bacterial-derived HA contain at most 0.12% contaminants which absorb at 280 nm. Since these same solutions contain almost no nucleic acid contamination, the purity is in the range of at least 99.88%. In this respect it is notable that amino acid analysis of similarly extracted HA indicated the presence of 0.04% protein. This would mean that the HA purity is as high as 99.96%. This is compared with the purity of commercially available rooster comb derived HA (HYLARTILS®) available from Pharmacia or Hyalovet® available from Trans Bussan) which, according to our tests, have purities in the range of 99.78% to 99.86% respectively.

TABLE II

PROTEIN AND NUCLEIC ACID CONTAMINATION OF 1.0% HYALURONIC ACID AS MEASURED BY UV SPECTROPHOTOMETRY

| | UV Absorbence | | Concentration | |
|---|---|---|---|---|
| Sample | O.D. at 280 nm | O.D. at 257 nm | Protein mg/ml | Nucleic Acid μg/ml |
| Ferm 1 | 0.45 | — | 0.66 | — |
| Ferm 2 | 0.83 | — | 1.22 | — |
| Ferm 3 | 0.75 | — | 1.10 | — |
| Ferm 4 | 0.47 | — | 0.69 | — |
| Miles Labs. (Rooster Comb) low purity | 1.16 | 1.31 | 1.70 | 48.5 |
| Pharmacia HULARTIL ® | 0.91 | 1.63 | 1.33 | 60.3 |
| Trans Bussan Hyalovet ® 1/30 dil. = 0.27 | 1.27 | >2.0 | 1.86 | >74 <300 |

Further studies on purity were conducted with the bacterial-derived HA. Effectiveness of two alcohol purification processes were followed spectrophotometrically at 280 nm, 257 nm, and 195 nm. Absorbence at 195 nm represents the actual absorbence of HA and is linearly related to concentration of HA. Table III shows optical density results whereas Table IV converts all readings to concentrations of protein, nucleic acid and HA. These two more purified lots yielded bacterial-derived HA which was 99.99% pure using either 95% ethanol (ETOH) or 99% isopropyl alcohol extraction.

TABLE III

PURIFICATION OF HYALURONIC ACID SOLUTIONS - UV ABSORBENCE

| | UV Absorbence | | | | | |
|---|---|---|---|---|---|---|
| | O.D. at 280 nm | | O.D. at 257 nm | | O.D. at 195 nm | |
| | ETOH | Isopropyl | ETOH | Isopropyl | ETOH | Isopropyl |
| 1st H₂O Solution | 0.480 | 0.442 | 0.456 | 0.341 | 0.740 | 0.643 |
| 2nd H₂O Solution | 0.215 | 0.288 | 0.204 | 0.230 | 1.00 | 0.898 |
| 3rd H₂O Solution | 0.215 | 0.155 | 0.191 | 0.182 | 1.76 | 1.82 |
| 4th H₂O Solution (Final 1%) | 0.078 | 0.070 | 0.140 | 0.120 | 1.90 | 1.82 |

TABLE IV

PROOF OF PURIFICATION - PROTEIN AND NUCLEIC ACID CONCENTRATIONS COMPARED WITH HYALURONIC ACID CONCENTRATION

| | Concentration | | | | | |
|---|---|---|---|---|---|---|
| Purification Step | Protein mg/ml | | Nucleic Acid g/ml | | Hyaluronic Acid mg/ml | |
| | ETOH | Isopropyl | ETOH | Isopropyl | ETOH | Isopropyl |
| 1st H₂O Solution | 0.52 | 0.66 | 17.3 | 12.8 | 4.0 | 3.5 |
| 2nd H₂O Solution | 0.32 | 0.44 | 7.6 | 8.5 | 5.4 | 4.9 |
| 3rd H₂O Solution | 0.32 | 0.22 | 7.0 | 6.9 | 9.3 | 9.8 |
| 4th H₂O Solution Solution (Final | 0.08 | 0.10 | 5.0 | 4.3 | 10.2 | 9.8 |

TABLE IV-continued
PROOF OF PURIFICATION - PROTEIN AND NUCLEIC ACID CONCENTRATIONS COMPARED WITH HYALURONIC ACID CONCENTRATION

| Purification Step | Protein mg/ml ETOH | Protein mg/ml Isopropyl | Nucleic Acid g/ml ETOH | Nucleic Acid g/ml Isopropyl | Hyaluronic Acid mg/ml ETOH | Hyaluronic Acid mg/ml Isopropyl |
|---|---|---|---|---|---|---|
| 1% HA in H$_2$O) | | | | | | |

Slab gel electrophoresis was used to further analyze the various 1.0% hyaluronic acid preparations listed in Table II for nucleic acids. Such a technique can differentiate DNA from RNA. A 0.8% low endosmosis agarose containing 2 μg/ml ethidium bromide was used in conjunction with short wave length UV light in order to visualize the nucleic acids after electrophoresis. DNA being of a much larger molecular weight remains near the origin whereas RNA migrates with the buffer front. Twenty-five μl samples were electrophoresed 18 hours at 90 volts in a Canalco Slab Gel apparatus. Results indicated no detectable nucleic acids in any of our four preparations or the HYLARTIL ® product. The Hyalovete product showed a significant amount of nucleic acid in the form of RNA.

Figure 5:
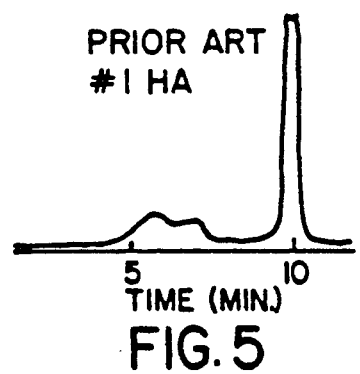
FIGS. 5–7 are graphs showing HPLC determined molecular weight distributions (retention times) of three commercially available prior art HA preparations.
Figure 6:
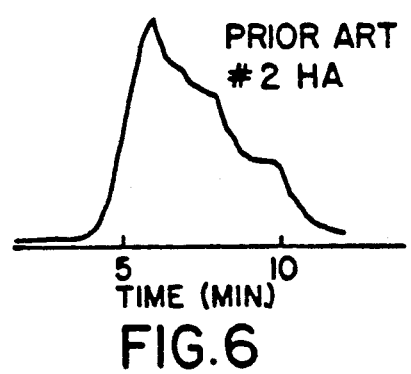
Figure 7:
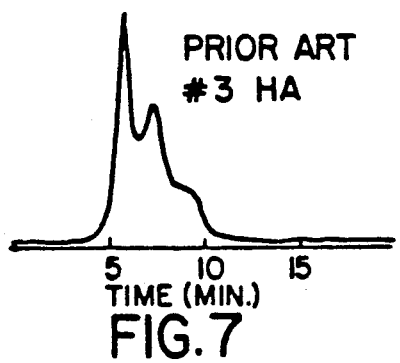

High Performance Liquid Chromatography (HPLC) was used to analyze the molecular weight of the various HA preparations. This is a newer and more accurate method than viscometry as mentioned in the U.S. Pat. No. 4,141,973. A Waters Micro Bondagel/E-High Å column was used for molecular weight determination. In this column it was impossible to run aqueous standards in the molecular weight range required along with test samples in order to determine accurate molecular weights. However, relative molecular weights based upon retention times on the column were determined. Theoretically, with this procedure, the earlier the time of peak detection the higher the molecular weight. The column had a retention time of 10 min. with minimum and maximum molecular weight capabilities between 15,000 and 7,000,000 daltons. FIGS. 1-4 show the HPLC tracings for our first four fermenter preparations. Miles Hyaluron, Pharmacia HYLARTIL ® and Trans Bussan Hyalovet are shown in FIGS. 5-7. The retention times of the peaks and shoulders were determined and relative molecular weights calculated based on a linear relationship between molecular weight (15,000 to 7,000,000 daltons) and retention time (0-10 minutes). Such relative molecular weights are listed in Table V. As can be seen in FIGS. 1-4, sodium hyaluronate obtained according to this disclosure gives an essentially single, substantially symmetrical high molecular weight (avg. higher than about 2,000,000 dalton) HPLC distribution peak. In FIGS. 1-4 at least about 98% of the HA molecules are within the single peaks shown. Such close control of high molecular weight distribution is not shown in existing commercial products as illustrated in FIGS. 5-7. FIG. 5 (Prior Art #1) illustrates the HPLC tracing for the Miles Hyaluron HA product. FIG. 6 (Prior Art #2) represents the Hyalovet product and FIG. 7 (Prior Art #3) represents the HYLARTIL ® product. It is thought that this close control of final molecular weight range may be due to the simplicity of the extraction procedure requiring minimal shear-producing steps as well as to the lack of hyaluronidase which could degrade high molecular weight HA.

TABLE V
Relative Molecular Weights of Hyaluronic Acid Moieties in Various Preparations

| Sample | Relative Molecular Weights in Millions Range | Relative Molecular Weights in Millions Average |
|---|---|---|
| Fermenter 1 | 2.2-3.9 | 2.8 |
| Fermenter 2 | 2.5-4.0 | 3.8 |
| Fermenter 3 | 1.7-2.8 | 2.4 |
| Fermenter 4 | 1.1-3.9 | 2.6 |
| Hyaluron | 0.015-3.0 | 0.015 |
| HYALOVET | <0.010-3.7 | .015, 1.8, 3.7 |
| HYLARTIL ® | <0.010-3.8 | 1.9 |

As noted above the relative molecular weight range of HA moieties found in bacterial-derived HA is narrow with the majority (98%) measuring between about 1,100,000 or 2,200,000 and 4,000,000 daltons. Via the same method, Hyalovet contains three distinct molecular weight moieties of 2,700,000; 1,700,000 and 300,000 daltons. Finally, the HYLARTIL ® product contained an array of HA molecular weights from 10,000 to 3,700,000 daltons. As shown, the HYLARTIL ® product contains the widest variation of molecular weight sizes.

From the various analytical tests described herein, it has been determined that HA extracted from bacteria via a simple method is purer than three commercial products made from either rooster combs or umbilical cords. The latter are produced via a complex process which is inefficient yielding only 0.079% HA. This is compared with HA extracted from streptococci which can reach yields as high as 50% w/w.

Joint Fluid Replacement

Hyaluronic acid prepared from bacteria as described herein has been tested for reactivity in tibiotarsal and radial-carpal joints of horses. The following clinical index test was devised in order to measure reactivity of HA preparations post intra-articular injection of horses.

The test protocol is as follows:
1. Assess normal movement of joint to be injected. Assign lameness indices from 0 to 5 according to the following definitions.

Lameness Index

0 = No lameness
1 = Slight lameness - moderate
2 = Noticeable lameness - moderate
3 = Obvious lameness
4 = Severe lameness - reluctant to move or bear weight
5 = Cannot bear weight. If down, animal is unable to rise.

2. Sedate horse (e.g. with Rompun sedative).
3. Shave hair around the joint area to be injected.
4. Determine Swelling Observation Index according to the following definitions.

Swelling Observation Index

0 = No Swelling
1 = Nothing obvious - palpable fluid
2 = Slightly noticeable - palpable fluid
3 = Noticeable swelling of entire joint
4 = Severe swelling at injection site
5 = Severe swelling involving more than the joint alone.

5. With cloth tape measure, measure joint circumference immediately anterior to the anterior aspect of the third metatarsal (tibiotarsal joint) or immediately distal to the protuberance of the accessory carpal bone that is around the radial carpal bone (carpal joint).

The exact circumference of the joint (in millimeters) before and after injection is recorded. A difference between the circumference each day post injection and the original circumference is calculated. If the difference is greater than 1.0 cm, the exact measurement is added to the other two index values in order to determine the clinical index.

6. Remove joint fluid (1.0–2.0 cc) prior to injection with a 3.0 cc syringe with a 20–22 ga. X 1" needle.
7. Inject joint with 2.0 cc of a 1% preparation of hyaluronic acid being evaluated for reactivity. For this injection, use a 3.0 cc syringe with the same needle (exchanging syringes only) as used to remove joint fluid. This is done so as to reduce trauma to the joint as much as possible.
8. Apply digital pressure to the injection site for 1 to 3 minutes after injection. This is done to prevent backflow of the very viscous HA.
9. Observations and measurements are made for four consecutive days post injection, then on day 7.
10. The Clinical Index (CI) is calculated as follows:

Total Lameness Index (TLI) = Sum of Daily Lameness Indices

Total Swelling Index (TSI) = Sum of Daily Swelling Observations + Sum of Joint Circumference Measurements Greater Than 1.0 cm.

CI = TLI + TSI

11. Interpretation

Joint injection alone causes trauma with development of some swelling and lameness. This was proven by evaluating numerous joints injected with phosphate buffered saline (PBS) and some joints in which only fluid was removed. CIs were calculated on these traumatized joints. They varied from 0 to 18.7 among 56 joints. However, the average CIs in the three separate studies of traumatized joints showing these wide individual variations were 0.7, 5.3, and 3.4. It is thus suggested that an average CI value of 6.0 or less in at least 10 joints could be expected from injection trauma. On this basis, we have assigned a 10 - joint average CI value of 6.0 or less as acceptable in the horse joint reactivity test for evaluation of HA preparations. Any product showing a 10 - joint average of CI of 6.0 is unacceptable. Using these criteria, several HA preparations were tested. Results are shown in Table VI.

TABLE VI

Evaluation of Hyaluronic Acid Preparations by the Horse Joint Reactivity Test

| Preparation | No. of Joints | Average CI | Acceptability of Preparation |
| --- | --- | --- | --- |
| Microbiological Source HA Filtered through Nitrocellulose | 14 | 4.6 | Acceptable |
| | 13 | 5.5 | Acceptable |
| Microbiological Source HA Non-filtered | 11 | 11.4 | Unacceptable |
| | 6 | 17.4 | Unacceptable |
| Prior Art #1 Purified and Unacceptable Filtered | 10 | 6.2 | |

The microbiological source HA listed in Table VI was that obtained from fermenters 1 through 4 as described previously. It is noteworthy that this material is acceptable for joint injection after nitrocellulose filtration but not prior to such filtration. On the other hand, Prior Art #1 (see FIG. 5) is on the borderline of being unacceptable even after nitrocellulose filtration. Evidently, the reactive proteinaceous load in the Prior Art #1 preparation is too great to be removed via the protein binding filtration step.

The same Clinical Index can be used to evaluate efficacy of treatment of diseased joints with HA. In this test system clinical symptoms are induced in joints with intraarticular injection of complete or incomplete Freund's adjuvant. This adjuvant produces first an acute and then a chronic pathology of the joint characterized by extreme lameness and swelling which does not appear to reverse itself within two months.

Some such efficacy studies have been conducted on the bacterial-derived HA.

Figure 8:
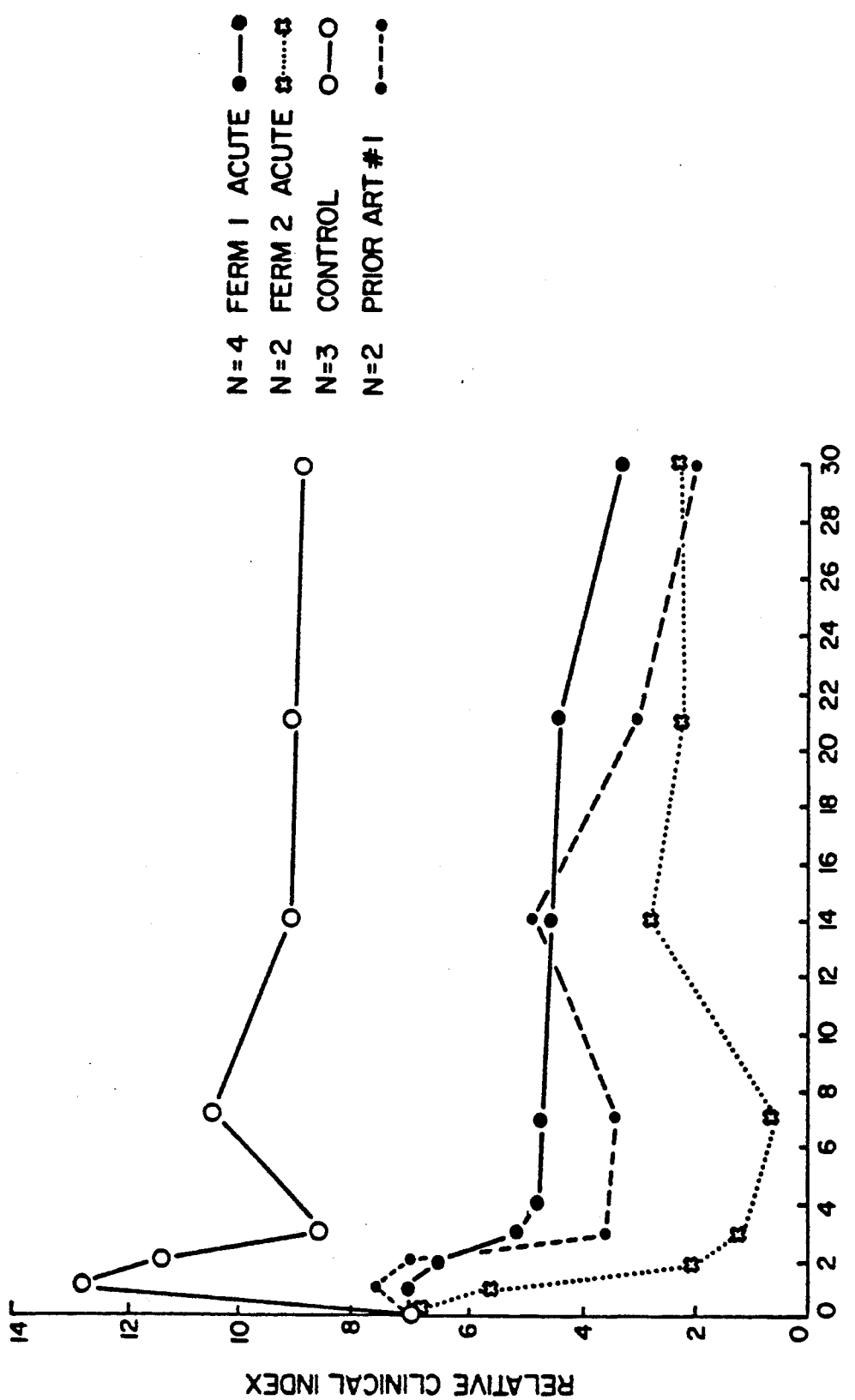

Experiments were designed to evaluate the effect of removing some of the joint fluid from adjuvant induced pathological joints and replacing it with bacterial-derived HA. This was done with both acute joints (HA injection within three days of the Freund's Complete Adjuvant injection) and with chronic joints (HA injected within 12 to 34 days of Freund's injection). Clinical Index evaluation was begun the day of adjuvant injection and continued for four days following the HA injection after which weekly observations were made for three weeks. FIGS. 8 and 9 display the results over 30 day periods.

FIG. 8 represents the acute situation. The zero day readings were all adjusted to seven on the relative index scale so that comparisons could be better visualized. Zero day represents three days post Freund's injection in the acute joints. FIG. 8 then portrays the change in Clinical Index for the first 30 days post injection with HA from fermenters 1 and 2 and Prior Art #1 after further purification. These results are compared with similar adjuvant injected joints left untreated (control). It is notable that the control horses continually worsen through day 4 post Freund's injection before showing some improvement on their own. However, this improvement does not reach the starting level by day three and by day four appears to be plateauing. This is the typical picture for induction of chronic pathology. A significant improvement in acute symptoms is observed after injection of HA.

The chronic situation is represented by FIG. 9. Horses which have been injected with Freund's Complete Adjuvant 12-34 days prior to HA treatment can serve as their own controls since these horses had been stable for at least seven days prior to day zero. The control line represents these control index levels. Again, immediate clinical improvement is noted after treatment with HA. Longer term observation of these horses has indicated that the improvement tends to plateau. Therefore, it is expected that more than one treatment may be necessary.

One horse entered the study with a diseased joint of unspecified cause. As indicated in FIG. 10, two injections of bacterial-derived HA were administered to this joint 30 days apart. In this case, the zero day readings were adjusted to 10 in order to display the complete treatment response. Immediate improvement was noted after both the first and second injections of HA. The improvement after the first injection was followed by some return of pathology as indicated by swelling only. After the second HA injection joint swelling was eliminated and has not returned within three months post treatment.

From the data presented herein it is obvious that ultra pure bacterial-derived HA is nonreactive in horse joints and displays efficacy for reversing lameness and/or swelling in diseased joints. Since bacterial-derived HA as described herein is purer than any commercially available product, including those used in opthalmalogical treatments, it is highly probable that these HA preparations could also be used to replace vitreous humor of the eye during surgery. They should be able to substitute for any other use applied to the rooster comb or umbilical cord HA.

The invention is further illustrated, but is not intended to be limited by the following examples in which all parts and percentages are by weight unless otherwise specified.

EXAMPLE 1

The virulence of a *Streptococcus equi* and therefore its hyaluronic acid production, which is a virulence factor, was enhanced by passaging through serologically negative horse blood. In particular, some pus from an abscess of a horse showing the symptoms of a *Streptococcus equi* infection, which was later established by differential sugar testing and staining to contain this microorganism, was incubated with some serologically negative horse blood (blood having no detectable levels of antibody against this microorganism) and the CDM described in the Van de Rijn and Kessler article, supra, for three hours at 37° C. A small aliquot was then placed on a blood agar plate (small petri dish with solid agar and small amount of medium containing blood) overnight at 37° C. The large mocioid colony was then transferred into a fresh mixture of serologically negative horse blood and CDM for three hours at 37° C. After a total of four incubations in horse blood/CDM the final isolated strain was grown in just CDM and a sample was submitted to the ATCC and received deposit number 39,506. This strain was substantially more virulent than the initial naturally occurring strain.

EXAMPLE 2

The strain developed in Example 1 was used to grow cultures for 22 and 64 hours and the hyaluronic acid generated was harvested and isolated. In particular these cultures were grown in a stirred vented vessel with air feed lines which simply compensate for the oxygen consumed by the microorganisms but do not "aerate" by vigorously adding air or oxygen in the same CDM as used in Example 1 at 37° C. with the pH initially set at 7.6 and thereafter controlled at a value of about 7.2. In the 64 hour culture I weight percent of dextrose, based on the total weight of culture, was added every twenty-four hours. For both cultures the pH control was terminated about sixteen hours before harvest.

Both cultures remained in the log or exponential growth phase for at least the period of pH control. This was apparent from the pH controller record which indicated additions approximately every five minutes and from optical density measurements which increased during the entire culturing period as follows:

| ITEM In Hours | 22 Hour Culture Optical Density | 64 Hour Culture Optical Density |
|---|---|---|
| 3 | 0.13 | 0.07 |
| 6 | 0.17 | 0.12 |
| 22 | 0.18 | 0.22 |
| 28 | | 0.22 |
| 30 | | 0.22 |
| 33 | | 0.235 |
| 38.5 | | 0.5 |
| 64 | | 0.675 (at 1:10 dilution) |

The lag in the sixty four hour culture was attributed to its exhausting the glucose in its medium before the next addition. It was surprising that a streptococcal organism could be kept in log phase in a CDM for an extended period. The only prior reported extended log phase growth for this genus of microorganisms appears to be an aerated Shaker Culture in a protein rich medium which is reported in Japanese Published Patent Application 56692-83.

Sodium hyaluronate was then harvested and isolated from each culture by the first technique described hereinabove involving ethanol precipitation followed by centrifugation and redissolution in water. However, in this case five precipitations with ethanol were utilized. The dry cell weight of each culture was estimated by designating one centrifugation pellet as a standard and then estimating the dry cell weight content from the pellet weight. The dry cell content and hyaluronic acid yield were as follows:

| Culture | Dry Cell Weight | Hyaluronic Acid Obtained | Yield Based on Dry Cell Weight |
|---|---|---|---|
| 22 Hour | 2.9 grams/10 l | 1.1 g/10 l | 37.9% |
| 64 Hour | 3.79 grams/10 l | 2.06 g/10 l | 54.4% |

Thus, the longer term culture is substantially more efficient in producing hyaluronic acid. However, subsequent experiments indicated that culturing for beyond 72 hours results in only marginal increases in yield evidently because nutrients other than glucose became depleted from the CDM.

EXAMPLE 3

Hyaluronic acid was harvested and isolated from a one hundred liter culture prepared in a manner similar to that described in Example 2. However, it was analyzed for protein content by UV absorption at 280 nanometers and nucleic acid content by UV absorption at 260 nanometers immediately before and immediately after passage through a single thickness 1.2 micrometer pore 293 mm diameter nitrocellulose filter. The 4.5 liters of aqueous sodium hyaluronate solution being treated had the following pre and post filtration contents:

| Contaminate | Pre Filtration Content | Post Filtration Content | Percent Reduction |
|---|---|---|---|
| Protein | 0.28 mg/ml | 0.06 mg/ml | 78% |
| Nucleic acids | 0.09 mg/ml | 0.023 mg/ml | 74% |

The protein load on the filter was about 1.88 mg/cm$^2$ and it removed approximately 1.48 mg/cm$^2$ of protein to effect a protein reduction of 78%. After one further ethanol precipitation and resolution this lot was found to contain 20.08 grams of sodium hyaluronate for a yield of about two grams per ten liters of original culture.

The degree of contaminate removal appeared to be related to the contaminate load on the nitrocellulose filter. In a similar experiment 7.5 liters of an aqueous sodium hyaluronate solution were passed through a similar filter. The protein reduction appeared to be about 43% and the nucleic acid reduction seemed to be about 29% but the protein load was about 4.25 mg/cm$^2$. The absolute removal was about 1.85 mg/cm$^2$ in reducing the concentration from 0.38 to 0.215 mg/ml. The absolute reduction in nucleic acid content was also similar between the two experiments with 0.045 mg/cm$^2$ removed from the 4.5 liter batch and 0.052 mg/cm$^2$ removed from the 7.5 liter batch.

EXAMPLE 4

An aqueous approximately one weight percent sodium hyaluronate solution displaying pyrogenicity in the rabbit test was rendered non-pyrogenic by treatment with strong acid washed activated carbon. The solution was contacted with 29 grams per liter Gelman 12011 a strong acid washed activated carbon with a surface area of about 700 m$^2$/g (thus giving 20,000 m$^2$/liter of surface area) for one and sixty minutes. A reference solution of lipopolysaccaride (LPS), the commonly suspected pyrogenic agent, was similarly treated. The LPS content of both was evaluated by Limulus amoebacyte lysate (LAL) analysis with the following results:

LPS CONTENT

|  | Initial Content | Post 1 minute Treatment | Post 60 minute Treatment |
|---|---|---|---|
| HA solution | 15.5 ng/ml | 12.08 ng/ml | 8.12 ng/ml |
| LPS solution | 30 ng/ml | 13.35 ng/ml | 12.75 ng/ml |

The results with the hyaluronate solution was confirmed by testing of similarly treated samples in the rabbit test.

The ability of activated carbon to extract LPS from an aqueous sodium hyaluronate solution appeared to be unique. Although other materials such as ion exchange resins and affinity binding columns marketed for LPS adsorption extracted LPS from a water solution they were unable to extract from an aqueous hyaluronate solution.

EXAMPLE 5

Hyaluronic acid was prepared using the strain of microorganism prepared in accordance with Example 1 by culturing a five hundred liter batch for forty-eight hours in accordance with the procedures of Example 2 except that a second glucose addition of 0.5 weight percent based on the total culture weight was made sixteen hours after each one percent addition by isolating and purifying the product by the second preferred procedure utilizing the "winder" which is discussed hereinabove. The procedure included the especially preferred features of lowering the viscosity by heat treatment, and filter sterilizing by passage through a 0.2 micrometer pore filter as well as a subsequent pyrogen treatment by passage at between 37° and 56° C. through a Gelman 12011 strong acid washed activated carbon filter providing 20,000 m surface area per liter of solution being treated. The final aqueous solution had a sodium hyaluronate content of 1.19 weight percent. This hyaluronic acid had a FPLC (fast protein liquid chromatography) determined average molecular weight of $1.88 \times 10^6$ daltons with a narrow essentially symmetrical single distribution peak, a 37° C. viscosity of 147 cSt, a nucleic acid content of less than 0.003 mg/ml by ethidium bromide fluorescence and a total amino acid content of less than 0.005 mg/ml by orthophthalaldehyde fluorescence. It caused no readily apparent antigenic reaction when injected into horses and gave a negative indication in the rabbit pyrogen test.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of high molecular weight hyaluronic acid with a narrow molecular weight distribution comprising
   a) increasing the virulence and the hyaluronic acid generating ability of an existing strain of *Streptococcus equi* by passaging it through serologically negative horse blood,
   b) growing a culture of the strain of a) in a medium free of extraneous protein in a defined medium,
   c) maintaining the culture in log phase growth for at least about 24 hours by
      i) maintaining the pH of the medium between about 7 and 7.2,
      ii) maintaining the temperature at about 37° C., and
      iii) feeding at least about one weight percent of glucose, based on the total culture weight to the medium no less frequently than about every 24 hours,
   d) separating the generated capsular hyaluronic acid from the cell walls by incubating the culture with at least about 0.01 weight percent, based on the total culture weight, or a sulphonate based anionic surfactant,
   e) precipitating the generated hyaluronic acid from the medium containing said anionic surfactant by the addition of an aliphatic quaternary ammonium salt,
   f) separating the precipitated hyaluronic acid from the anionic surfactant and ammonium salt by dissolving it in a high molarity aqueous solution of a calcium salt, g) precipitating the hyaluronic acid from the calcium salt solution by combining the solution with a lower alcohol selected from the group consisting of ethanol and isopropanol, h) repeatedly redissolving the reprecipitated hyaluronic acid in water, adding sufficient sodium chloride to provide at least about ten grams per liter and reprecipitating the hyaluronic acid by combining the solution with ethanol or isopropanol, i) passing an aqueous solution of the repeatedly dissolved and precipitated hyaluronic acid through a nitrocellulose filter, and j) treating an aqueous solution of the repeatedly dissolved and precipitated hyaluronic acid with sufficient strong acid washed activated carbon to remove any pyrogen from said hyaluronic acid as measured by the rabbit pyrogen test.

2. A process for the production of high molecular weight hyaluornic acid comprising a) growing a microorganism having all of the identifying characteristics of the strain of *Streptococcus equi* ATCC Number 39506 in an aqueous chemically defined medium which is free of protein not released by the microorganism, b) inactivating any extracellular hyaluronidase generated by the microorganism, c) maintaining the microorganism to essentially log phase growth for in excess of about 24 hours by
  i) maintaining the pH in the range of between about 7 and 7.2 by continuous or intermittent addition of base,
  ii) maintaining the temperature in the range of about 37° C., and
  iii) adjusting the glucose content of the medium to at least one weight percent at least every 24 hours, d) isolating the generated hyaluronic acid from the culture without disrupting the streptoccoccal cells, and e) purifying the isolated hyaluronic acid without causing any significant molecular weight degradation.

* * * * *